US007361741B2

(12) United States Patent
Bezemer et al.

(10) Patent No.: US 7,361,741 B2
(45) Date of Patent: Apr. 22, 2008

(54) ANTIBODY, OR FRAGMENT THEREOF, CAPABLE OF BINDING SPECIFICALLY TO HUMAN PANCREATIC LIPASE

(75) Inventors: Sandra Bezemer, Vlaardingen (NL); Monique Van Der Burg, Vlaardingen (NL); Johannes Joseph De Haard, Vlaardingen (NL); Erwin Tareilus, Vlaardingen (NL)

(73) Assignee: Lipton, division of Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 09/805,290

(22) Filed: Mar. 13, 2001

(65) Prior Publication Data

US 2004/0002583 A1 Jan. 1, 2004

(30) Foreign Application Priority Data

Mar. 14, 2000 (EP) .................................. 00200930

(51) Int. Cl.
*C07K 16/00* (2006.01)
*C07K 16/40* (2006.01)

(52) U.S. Cl. .............................. 530/388.1; 530/388.26

(58) Field of Classification Search ............. 530/387.1, 530/388.1, 388.2; 424/130.1, 146.1
See application file for complete search history.

(56) References Cited

U.S. PATENT DOCUMENTS 6,558,936 B1 * 5/2003 Khodadoust et al. ....... 435/198

FOREIGN PATENT DOCUMENTS

| EP | 0 584 421 | 3/1994 |
| WO | 94/01567 | 1/1994 |
| WO | 94/04678 | 3/1994 |
| WO | 94/25591 | 11/1994 |
| WO | 97/49805 | 12/1997 |
| WO | 98/34630 | 8/1998 |
| WO | 98/56928 | 12/1998 |
| WO | 99/46300 | 9/1999 |

OTHER PUBLICATIONS

Ngo et al. The Protein Folding Problem and Tertiary Structure Prediction. Merz and LeGrand, Eds. Birkhauser Boston 1994, pp. 491-495.*
Database Embase Accession No. 1998286804, 1998, (Abstract of Acta Chirurgica Austriaca, 30/3, 141-143), one page.*
Lauwereys et al (The EMBO Journal, 13: 3512-3520, 1998).*
Davies and Riechmann (Biotechnology, 13: 475-479, 1995).*
S. Bezzine et al.: "Human pancreatic lipase: an exposed hydrophobic loop from the C-terminal domain may contribute to interfacial binding." BIOCHEMISTRY, vol. 37, No. 34, Aug. 25, 1998, pp. 11846-11855.
M Lowe et al.: "Cloning and characterization of human pancreatic lipase cDNA." The Journal of Biological Chemistry, vol. 264, No. 33, Nov. 25, 1989, pp. 20042-20048.
F. Martin et al.: "Affinity selection of a camelized VH domain antibody inhibitor of hepatitis C virus NS3 protease." Protein Engineering, vol. 10, No. 5, 1997, pp. 607-614.
M. Arbabi-Ghahroudi et al.: "Selection and identification of single domain antibody fragments from camel heavy-chain antibodies." FEBS Letters, vol. 414, Sep. 15, 1997, pp. 521-526.
Aoubala et al., The Journal of Biological Chemistry, vol. 8, 1995, pp. 3932-3937.

* cited by examiner

*Primary Examiner*—Christina Chan
*Assistant Examiner*—Marianne DiBrino
(74) *Attorney, Agent, or Firm*—Gerard J. McGowan, Jr.

(57) ABSTRACT

An antibody, or fragment thereof, capable of binding specifically to one or more human dietary enzymes, said antibody or fragment thereof comprising a heavy chain variable domain derived from an immunoglobulin naturally devoid of light chains, or a functional equivalent thereof.

3 Claims, 4 Drawing Sheets

```
                     SEQUENCE LISTING

<160> NUMBER OF SEQ ID NOS: 34

<210> SEQ ID NO 1
<211> LENGTH: 13
<212> TYPE: PRT
<213> ORGANISM: lama sp.

<400> SEQUENCE: 1

Ala Arg Ser Leu Val Gln Thr Pro Thr Ser Tyr Asp Tyr
 1               5                  10

<210> SEQ ID NO 2
<211> LENGTH: 13
<212> TYPE: PRT
<213> ORGANISM: lama sp.

<400> SEQUENCE: 2

Ala Arg Ser Leu Val Leu Thr Pro Thr Ser Tyr Asp Tyr
 1               5                  10

<210> SEQ ID NO 3
<211> LENGTH: 13
<212> TYPE: PRT
<213> ORGANISM: lama sp.

<400> SEQUENCE: 3

Ala Arg Ser Leu Glu Gln Thr Pro Thr Ser Tyr Asp Tyr
 1               5                  10

<210> SEQ ID NO 4
<211> LENGTH: 13
<212> TYPE: PRT
<213> ORGANISM: lama sp.

<400> SEQUENCE: 4

Ala Arg Ser Leu Glu Leu Thr Pro Thr Ser Tyr Asp Tyr
 1               5                  10

<210> SEQ ID NO 5
<211> LENGTH: 12
<212> TYPE: PRT
<213> ORGANISM: lama sp.

<400> SEQUENCE: 5

Arg Gly Gly Leu Thr Gln Tyr Ser Glu His Asp Tyr
 1               5                  10
```

<210> SEQ ID NO 6
<211> LENGTH: 7
<212> TYPE: PRT
<213> ORGANISM: lama sp.

<400> SEQUENCE: 6

Thr Gly Ala Glu Gly His Tyr
 1               5

<210> SEQ ID NO 7
<211> LENGTH: 11
<212> TYPE: PRT
<213> ORGANISM: lama sp.

<400> SEQUENCE: 7

Thr Asp Met Gly Arg Tyr Gly Thr Ser Glu Trp
 1               5                  10

<210> SEQ ID NO 8
<211> LENGTH: 13
<212> TYPE: PRT
<213> ORGANISM: lama sp.

<400> SEQUENCE: 8

Asp Val Arg Pro Tyr Arg Thr Ser Arg Tyr Leu Glu Val
 1               5                  10

<210> SEQ ID NO 9
<211> LENGTH: 13
<212> TYPE: PRT
<213> ORGANISM: lama sp.

<400> SEQUENCE: 9

Asp Val Arg Pro Tyr Arg Thr Ser Arg Tyr Leu Glu Leu
 1               5                  10

<210> SEQ ID NO 10
<211> LENGTH: 13
<212> TYPE: PRT
<213> ORGANISM: lama sp.

<400> SEQUENCE: 10

Asp Val Arg Pro Tyr Arg Thr Ser Arg Tyr Leu Glu Ile
 1               5                  10

<210> SEQ ID NO 11
<211> LENGTH: 13
<212> TYPE: PRT
<213> ORGANISM: lama sp.

<400> SEQUENCE: 11

Gln Val Arg Val Arg Phe Ser Ser Asp Tyr Thr Asn Tyr
 1               5                  10

<210> SEQ ID NO 12
<211> LENGTH: 13
<212> TYPE: PRT
<213> ORGANISM: lama sp.

<400> SEQUENCE: 12

Leu Ile Arg Arg Lys Phe Thr Ser Glu Tyr Asn Glu Tyr
 1               5                  10

```
<210> SEQ ID NO 13
<211> LENGTH: 12
<212> TYPE: PRT
<213> ORGANISM: lama sp.

<400> SEQUENCE: 13

Leu Ile Thr Arg Trp Asp Lys Ser Val Asn Asp Tyr
 1               5                  10

<210> SEQ ID NO 14
<211> LENGTH: 12
<212> TYPE: PRT
<213> ORGANISM: lama sp.

<400> SEQUENCE: 14

Arg Arg Ser Asn Tyr Asp Arg Ser Trp Gly Asp Tyr
 1               5                  10

<210> SEQ ID NO 15
<211> LENGTH: 12
<212> TYPE: PRT
<213> ORGANISM: lama sp.

<400> SEQUENCE: 15

Leu Ile Ser Ser Tyr Asp Gly Ser Trp Asn Asp Tyr
 1               5                  10

<210> SEQ ID NO 16
<211> LENGTH: 14
<212> TYPE: PRT
<213> ORGANISM: lama sp.

<400> SEQUENCE: 16

His Ile Thr Pro Ala Gly Ser Ser Asn Tyr Val Tyr Gly Tyr
 1               5                  10

<210> SEQ ID NO 17
<211> LENGTH: 13
<212> TYPE: PRT
<213> ORGANISM: lama sp.

<400> SEQUENCE: 17

Asp Ile Arg Lys Arg Phe Thr Ser Gly Tyr Ser His Tyr
 1               5                  10

<210> SEQ ID NO 18
<211> LENGTH: 129
<212> TYPE: PRT
<213> ORGANISM: lama sp.

<400> SEQUENCE: 18

Gln Val Gln Leu Gln Asp Ser Gly Gly Gly Leu Val Gln Ala Gly Gly
 1               5                  10                  15

Ser Leu Arg Leu Ser Cys Ala Ala Ser Gly Ser Ile Phe Ser Ser Asp
                20                  25                  30

Leu Met Gly Trp Tyr Arg Gln Ala Pro Gly Lys Glu Arg Glu Ala Val
            35                  40                  45

Ala Arg Ile Thr Arg Gly Gly Thr Thr Ser Tyr Ala Asp Ser Val Lys
        50                  55                  60

Gly Arg Phe Thr Ile Ser Arg Asp Asn Ala Lys Asn Thr Met Tyr Leu
 65                  70                  75                  80

Gln Met Asn Ser Leu Lys Pro Glu Asp Thr Ala Val Tyr Tyr Cys Asn
                85                  90                  95
```

```
Ala Arg Arg Ser Asn Tyr Asp Arg Ser Trp Gly Asp Tyr Trp Gly Gln
            100                 105                 110

Gly Thr Gln Val Thr Val Ser Ser Ala His His Ser Glu Asp Pro Ser
        115                 120                 125

Ser

<210> SEQ ID NO 19
<211> LENGTH: 130
<212> TYPE: PRT
<213> ORGANISM: lama sp.

<400> SEQUENCE: 19

Gln Val Gln Leu Gln Glu Ser Gly Gly Gly Leu Val Gln Ala Gly Gly
 1               5                   10                  15

Ser Leu Arg Leu Ser Cys Ala Ala Ser Gly Ser Ile Gly Ser Ile His
            20                  25                  30

Thr Met Gly Trp Tyr Arg Gln Thr Pro Gly Lys Glu Arg Asp Val Val
        35                  40                  45

Ala Thr Ile Gln Asp Gly Gly Ser Thr Asn Tyr Ala Asp Ser Val Lys
    50                  55                  60

Gly Arg Phe Thr Ile Ser Arg Asp Asn Thr Leu Asn Thr Val Tyr Leu
65                  70                  75                  80

Gln Met Asn Asp Leu Lys Pro Glu Asp Thr Ala Val Tyr Tyr Cys Asn
                85                  90                  95

Ala Asp Val Arg Pro Tyr Arg Thr Ser Arg Tyr Leu Glu Val Trp Gly
            100                 105                 110

Gln Gly Thr Leu Val Thr Val Ser Ser Glu Pro Lys Thr Pro Lys Pro
        115                 120                 125

Gln Pro
    130

<210> SEQ ID NO 20
<211> LENGTH: 129
<212> TYPE: PRT
<213> ORGANISM: lama sp.

<400> SEQUENCE: 20

Gln Val Gln Leu Gln Glu Ser Gly Gly Gly Leu Val Gln Ala Gly Gly
 1               5                   10                  15

Ser Leu Arg Leu Ser Cys Ala Ala Ser Gly Thr Ile Leu Ser Ile Ile
            20                  25                  30

Tyr Met Asp Trp Tyr Arg Gln Thr Pro Gly Lys Gln Arg Glu Leu Val
        35                  40                  45

Gly Arg Ile Thr Ala Gly Gly Ser Thr Asn Tyr Ala Asp Ser Ala Lys
    50                  55                  60

Gly Arg Phe Thr Ile Ser Lys Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Leu Ile Thr Arg Trp Asp Lys Ser Val Asn Asp Tyr Trp Gly Gln
            100                 105                 110

Gly Thr Gln Val Thr Val Ser Ser Glu Pro Lys Thr Pro Lys Pro Gln
        115                 120                 125

Pro
```

<210> SEQ ID NO 21
<211> LENGTH: 130
<212> TYPE: PRT
<213> ORGANISM: lama sp.

<400> SEQUENCE: 21

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Gly Ser Ile His
            20                  25                  30

Thr Met Gly Trp Tyr Arg Gln Thr Pro Gly Thr Glu Arg Asp Val Val
        35                  40                  45

Ala Thr Ile Gln Asp Gly Gly Ser Thr Asn Tyr Ala Asp Ser Val Lys
    50                  55                  60

Gly Arg Phe Thr Ile Ser Arg Asp Asn Ile Leu Asn Thr Val Tyr Leu
65                  70                  75                  80

Gln Met Asn Ser Leu Lys Pro Glu Asp Thr Ala Val Tyr His Cys Asn
                85                  90                  95

Ala Asp Val Arg Pro Tyr Arg Thr Ser Arg Tyr Leu Glu Leu Trp Gly
            100                 105                 110

Gln Gly Thr Leu Val Thr Val Ser Ser Glu Pro Lys Thr Pro Lys Pro
        115                 120                 125

Gln Pro
    130

<210> SEQ ID NO 22
<211> LENGTH: 131
<212> TYPE: PRT
<213> ORGANISM: lama sp.

<400> SEQUENCE: 22

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ser Ser Ile Asn
            20                  25                  30

Val Met Gly Trp Phe Arg Gln Ala Pro Gly Lys Gln Arg Glu Leu Val
        35                  40                  45

Ala Ser Ile Thr Ser Gly Gly Ser Thr Asn Tyr Ala Asp Ser Leu Lys
    50                  55                  60

Gly Arg Phe Thr Ile Ser Arg Asp Asn Ala Lys Asn Ala Val Tyr Leu
65                  70                  75                  80

Gln Met Asn Asn Leu Lys Pro Glu Asp Thr Ala Val Tyr Tyr Cys Asn
                85                  90                  95

Ala His Ile Thr Pro Ala Gly Ser Ser Asn Tyr Val Tyr Gly Tyr Trp
            100                 105                 110

Gly His Gly Thr Lys Val Thr Val Ser Ser Glu Pro Lys Thr Pro Lys
        115                 120                 125

Pro Gln Pro
    130

<210> SEQ ID NO 23
<211> LENGTH: 130
<212> TYPE: PRT
<213> ORGANISM: lama sp.

<400> SEQUENCE: 23

Gln Val Gln Leu Gln Asp Ser Gly Gly Gly Leu Val Gln Ala Gly Gly
1               5                   10                  15

-continued

```
Ser Leu Arg Leu Ser Cys Ala Ala Ser Gly Thr Ile Gly Asp Ile Tyr
            20                  25                  30

Thr Met Ala Trp His Arg Gln Ala Pro Gly Lys Glu Arg Glu Leu Val
        35                  40                  45

Ala Ser Ala Thr Glu Ser Gly Ser Pro Asn Tyr Ala Asp Pro Val Lys
    50                  55                  60

Gly Arg Phe Thr Ile Ser Arg Asp Asn Gly Lys Leu Thr Val Tyr Leu
65                  70                  75                  80

Gln Met Asn Ser Leu Lys Pro Glu Asp Thr Ala Val Tyr Tyr Cys Asn
                85                  90                  95

Ala Leu Ile Arg Arg Lys Phe Thr Ser Glu Tyr Asn Glu Tyr Trp Gly
            100                 105                 110

Gln Gly Thr Gln Val Thr Val Ser Ser Glu Pro Lys Thr Pro Lys Pro
        115                 120                 125

Gln Pro
    130

<210> SEQ ID NO 24
<211> LENGTH: 130
<212> TYPE: PRT
<213> ORGANISM: lama sp.

<400> SEQUENCE: 24

Gln Val Gln Leu Gln Asp Ser Gly Gly Gly Leu Val Gln Thr Gly Gly
1               5                   10                  15

Ser Leu Arg Leu Ser Cys Ala Ala Ser Gly Pro Ile Gly Asp Val Tyr
            20                  25                  30

Leu Met Gly Trp Tyr Arg Gln Ala Pro Gly Lys Gln Arg Glu Met Val
        35                  40                  45

Ala Ser Ile Thr Ala Thr Gly Pro Pro Asn Tyr Thr Asp Ser Val Lys
    50                  55                  60

Gly Arg Phe Thr Ile Ser Arg Asp Asn Asp Lys Asn Thr Glu Tyr Leu
65                  70                  75                  80

Gln Met Asn Asn Leu Lys Pro Glu Asp Thr Ala Val Tyr Tyr Cys Asn
                85                  90                  95

Ala Gln Val Arg Val Arg Phe Ser Ser Asp Tyr Thr Asn Tyr Trp Gly
            100                 105                 110

Gln Gly Thr Gln Val Thr Val Ser Ser Glu Pro Lys Thr Pro Lys Pro
        115                 120                 125

Gln Pro
    130

<210> SEQ ID NO 25
<211> LENGTH: 129
<212> TYPE: PRT
<213> ORGANISM: lama sp.

<400> SEQUENCE: 25

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Arg Ser Ile Ser
            20                  25                  30

Ile Met Thr Trp Tyr Arg Gln Ala Pro Gly Lys Glu Arg Glu Leu Val
        35                  40                  45

Ala Arg Met Ser Ser Asp Gly Thr Thr Ser Tyr Thr Asp Ser Met Lys
    50                  55                  60
```

Gly Arg Phe Thr Ile Ser Arg Asp Asn Ala Lys Asn Thr Val Tyr Leu
65                  70                  75                  80

His Met Asn Asn Leu Lys Pro Glu Asp Thr Ala Val Tyr Tyr Cys Lys
                85                  90                  95

Ala Leu Ile Ser Ser Tyr Asp Gly Ser Trp Asn Asp Tyr Gly Gly Gln
            100                 105                 110

Gly Thr Gln Val Thr Val Ser Ser Glu Pro Lys Thr Pro Lys Pro Gln
        115                 120                 125

Pro

<210> SEQ ID NO 26
<211> LENGTH: 130
<212> TYPE: PRT
<213> ORGANISM: lama sp.

<400> SEQUENCE: 26

Gln Val Gln Leu Gln Asp Ser Gly Gly Gly Leu Val Gln Ala Gly Gly
1               5                   10                  15

Ser Leu Arg Leu Ser Cys Ala Ala Ser Gly Ser Ile Gly Asp Ile His
            20                  25                  30

Thr Met Gly Trp Tyr Arg Gln Thr Pro Gly Lys Gln Arg Asp Val Val
        35                  40                  45

Ala Thr Ile Gln Ser Gly Gly Ser Thr Asn Tyr Ala Asp Ser Val Lys
    50                  55                  60

Gly Arg Phe Thr Ile Ser Arg Asp Asn Thr Leu Asn Thr Val Tyr Leu
65                  70                  75                  80

Gln Met Asn Asp Leu Lys Pro Glu Asp Thr Gly Val Tyr Tyr Trp Asn
                85                  90                  95

Ala Asp Val Arg Pro Tyr Arg Thr Ser Arg Tyr Leu Glu Ile Trp Gly
            100                 105                 110

Gln Gly Thr Leu Val Thr Val Phe Leu Glu Pro Lys Thr Pro Lys Pro
        115                 120                 125

Gln Pro
    130

<210> SEQ ID NO 27
<211> LENGTH: 130
<212> TYPE: PRT
<213> ORGANISM: lama sp.

<400> SEQUENCE: 27

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Asp Phe Arg Tyr Asn
            20                  25                  30

Thr Met Ala Trp Tyr Arg Gln Ala Pro Gly Lys Gln Arg Glu Leu Val
        35                  40                  45

Ala Thr Ile Ala Ser Thr Tyr Arg Thr Ser Tyr Ala Asp Ser Val Lys
    50                  55                  60

Gly Arg Phe Thr Ile Ser Arg Asp Asn Ala Arg Gly Thr Val Tyr Leu
65                  70                  75                  80

Gln Met Asn Ser Leu Lys Pro Glu Asp Thr Ala Val Tyr Tyr Cys Ala
                85                  90                  95

Ala Ala Arg Ser Leu Val Gln Thr Pro Thr Ser Tyr Asp Tyr Trp Gly
            100                 105                 110

```
Gln Gly Thr Gln Val Thr Val Ser Ser Ala His His Ser Glu Asp Pro
        115                 120                 125
Ser Ser
    130

<210> SEQ ID NO 28
<211> LENGTH: 129
<212> TYPE: PRT
<213> ORGANISM: lama sp.

<400> SEQUENCE: 28

Gln Val Gln Leu Gln Glu Ser Gly Gly Gly Leu Val Gln Ala Gly Gly
  1               5                  10                  15

Ser Leu Arg Leu Ser Cys Ala Ala Ser Gly Ser Thr Phe Ser Phe Asn
             20                  25                  30

Ala Met Gly Trp Tyr Arg Gln Val Pro Gly Lys Gln Arg Glu Leu Val
         35                  40                  45

Ala Ala Ile Gly Asn Asp Gly Ala Thr Tyr Tyr Val Asp Ser Val Lys
     50                  55                  60

Gly Arg Phe Thr Ile Ala Arg Glu Asn Ala Lys Asn Thr Val Tyr Leu
 65                  70                  75                  80

Gln Met Ser Ser Leu Lys Pro Glu Asp Thr Ala Val Tyr Tyr Cys Lys
                 85                  90                  95

Gly Arg Gly Gly Leu Thr Gln Tyr Ser Glu His Asp Tyr Trp Gly Gln
            100                 105                 110

Gly Thr Gln Val Thr Val Ser Ser Glu Pro Lys Thr Pro Lys Pro Gln
        115                 120                 125

Pro

<210> SEQ ID NO 29
<211> LENGTH: 124
<212> TYPE: PRT
<213> ORGANISM: lama sp.

<400> SEQUENCE: 29

Gln Val Gln Leu Gln Glu Ser Gly Gly Gly Leu Val Gln Thr Gly Gly
  1               5                  10                  15

Ser Leu Arg Leu Ser Cys Ala Ala Ser Gly Ser Ile Gly Ser Met Tyr
             20                  25                  30

Val Leu Ser Trp Tyr Arg Gln Ala Pro Gly Lys Gln Arg Glu Pro Val
         35                  40                  45

Ala Ala Leu Met Gly Ser Gly Ser Thr Thr Tyr Ala Asp Ser Val Lys
     50                  55                  60

Gly Arg Phe Thr Ile Ser Arg Asp Asn Ile Lys Asn Thr Met Tyr Leu
 65                  70                  75                  80

Gln Met Asn Ser Leu Thr Pro Glu Asp Thr Gly Val Tyr Tyr Cys Ala
                 85                  90                  95

Gly Thr Gly Ala Glu Gly His Tyr Trp Gly Gln Gly Thr Gln Val Thr
            100                 105                 110

Val Ser Ser Ala His His Ser Glu Asp Pro Ser Ser
        115                 120

<210> SEQ ID NO 30
<211> LENGTH: 124
<212> TYPE: PRT
<213> ORGANISM: lama sp.

<400> SEQUENCE: 30
```

```
Gln Val Gln Leu Gln Glu Ser Gly Gly Gly Leu Val Gln Ala Gly Gly
 1               5                  10                  15

Ser Leu Arg Leu Ser Cys Ala Ala Ser Gly Ser Ile Gly Ser Leu Tyr
            20                  25                  30

Val Met Ser Trp Tyr Arg Gln Ala Pro Gly Lys Gln Arg Glu Pro Val
        35                  40                  45

Ala Ala Leu Met Gly Ser Gly Ser Thr Thr Tyr Ala Asp Ser Val Lys
    50                  55                  60

Gly Arg Phe Thr Ile Ser Arg Asp Asn Ile Lys Asn Thr Met Tyr Leu
65                  70                  75                  80

Gln Met Asn Ser Leu Lys Pro Glu Asp Thr Gly Val Tyr Tyr Cys Ala
                85                  90                  95

Gly Thr Gly Ala Glu Gly His Tyr Trp Gly Gln Gly Thr Gln Val Thr
            100                 105                 110

Val Ser Ser Glu Pro Lys Thr Pro Lys Pro Gln Pro
        115                 120
```

<210> SEQ ID NO 31
<211> LENGTH: 129
<212> TYPE: PRT
<213> ORGANISM: lama sp.

<400> SEQUENCE: 31

```
Gln Val Gln Leu Gln Glu Ser Gly Gly Asp Leu Val Gln Ala Gly Gly
 1               5                  10                  15

Ser Leu Arg Leu Ala Cys Ala Ala Ser Gly Ser Thr Phe Ser Phe Asn
            20                  25                  30

Ala Met Gly Trp Tyr Arg Gln Val Pro Gly Lys Gln Arg Glu Leu Val
        35                  40                  45

Ala Ala Ile Gly Asn Asp Gly Ser Thr Tyr Tyr Val Asn Ser Val Lys
    50                  55                  60

Gly Arg Phe Thr Ile Ser Arg Glu Asn Ala Lys Asn Thr Val Tyr Leu
65                  70                  75                  80

Gln Met Asn Ser Leu Lys Pro Glu Asp Thr Ala Val Tyr Tyr Cys Lys
                85                  90                  95

Gly Arg Gly Gly Leu Thr Gln Tyr Ser Glu His Asp Tyr Trp Gly Gln
            100                 105                 110

Gly Thr Gln Val Thr Val Ser Ser Glu Pro Lys Thr Pro Lys Pro Gln
        115                 120                 125

Pro
```

<210> SEQ ID NO 32
<211> LENGTH: 128
<212> TYPE: PRT
<213> ORGANISM: lama sp.

<400> SEQUENCE: 32

```
Gln Val Gln Leu Gln Glu Ser Gly Gly Gly Leu Val Gln Ala Gly Gly
 1               5                  10                  15

Ser Leu Arg Leu Ser Cys Thr Ala Ser Gly Thr Thr Asp Asn Ile Asn
            20                  25                  30

Ala Met Gly Trp Tyr Arg Gln Ala Pro Gly Lys Gln Arg Glu Leu Val
        35                  40                  45

Ala Ala Ile Ser Ser Gly Gly Asp Thr Tyr Tyr Thr Glu Phe Val Lys
    50                  55                  60
```

```
Gly Arg Phe Thr Ile Ser Arg Asp Asn Ala Lys Lys Ala Val Tyr Leu
 65                  70                  75                  80

Gln Met Asn Asn Leu Lys Ser Glu Asp Thr Ala Val Tyr Ser Cys Lys
                 85                  90                  95

Met Thr Asp Met Gly Arg Tyr Gly Thr Ser Glu Trp Trp Gly Gln Gly
            100                 105                 110

Thr Gln Val Thr Val Ser Ser Glu Pro Lys Thr Pro Lys Pro Gln Pro
            115                 120                 125
```

<210> SEQ ID NO 33
<211> LENGTH: 124
<212> TYPE: PRT
<213> ORGANISM: lama sp.

<400> SEQUENCE: 33

```
Gln Val Gln Leu Gln Glu Ser Gly Gly Gly Leu Val Gln Ala Gly Gly
  1               5                  10                  15

Ser Leu Arg Leu Ser Cys Ala Ala Ser Gly Ser Ile Gly Ser Met Tyr
                 20                  25                  30

Val Met Ser Trp Tyr Arg Gln Ala Pro Gly Lys Glu Arg Glu Pro Ile
             35                  40                  45

Ala Ala Leu Met Gly Ser Gly Ser Thr Thr Tyr Ala Asp Ser Val Lys
         50                  55                  60

Gly Arg Phe Thr Ile Ser Arg Asp Asn Glu Lys Asn Thr Met Tyr Leu
 65                  70                  75                  80

Gln Met Asn Ser Leu Thr Pro Glu Asp Thr Gly Val Tyr Tyr Cys Ala
                 85                  90                  95

Gly Thr Gly Ala Glu Gly His Tyr Trp Gly Gln Gly Thr Gln Val Thr
            100                 105                 110

Val Ser Ser Glu Pro Lys Thr Pro Lys Pro Gln Pro
            115                 120
```

<210> SEQ ID NO 34
<211> LENGTH: 130
<212> TYPE: PRT
<213> ORGANISM: lama sp.

<400> SEQUENCE: 34

```
Gln Val Gln Leu Gln Glu Ser Gly Gly Gly Leu Val Gln Ala Gly Gly
  1               5                  10                  15

Ser Leu Arg Leu Ser Cys Ala Ala Ser Gly Ser Asp Phe Arg Tyr Asn
                 20                  25                  30

Ala Met Ala Trp Tyr Arg Gln Ala Pro Gly Lys Gln Arg Lys Leu Val
             35                  40                  45

Ala Thr Ile Thr Tyr Thr Tyr Arg Thr Asn Tyr Ala Asp Ser Val Lys
         50                  55                  60

Gly Arg Phe Thr Ile Ser Arg Asp Asn Ala Arg Gly Thr Val Tyr Leu
 65                  70                  75                  80

Gln Met Asn Ser Leu Lys Pro Glu Asp Thr Ala Val Tyr Tyr Cys Ala
                 85                  90                  95

Ala Ala Arg Ser Leu Glu Leu Thr Pro Thr Ser Tyr Asp Tyr Trp Gly
            100                 105                 110

Gln Gly Thr Gln Val Thr Val Ser Ser Glu Pro Lys Thr Pro Lys Pro
            115                 120                 125

Gln Pro
130
```

ANTIBODY, OR FRAGMENT THEREOF, CAPABLE OF BINDING SPECIFICALLY TO HUMAN PANCREATIC LIPASE

CROSS REFERENCE TO RELATED APPLICATIONS

Not Applicable.

STATEMENT REGARDING FEDERALLY SPONSORED RESEARCH OR DEVELOPMENT

Not Applicable.

INCORPORATION-BY-REFERENCE OF MATERIAL SUBMITTED ON A COMPACT DISC

Not Applicable.

FIELD OF THE INVENTION

The present invention is in the field of applied biotechnology and relates in particular to the inhibition of human lipase.

BACKGROUND OF THE INVENTION

Cardiovascular diseases are the number one cause of death in the Western World. Epidemeologic and experimental data show clearly that high serum cholesterol levels, more precise high level of Low Density Lipoprotein particles, which contain cholesterol show a strong correlation with the occurrence of cardiovascular diseases. It is also well known that foods products containing fats high in saturated fatty acids contribute to high serum Low Density Lipoprotein levels. It has also be stated that hydrolysis of dietary fats, thereby liberating fatty acids in the stomach and intestinal tract increases the adsorption of cholesterol by the epithelial cells of the intestinal tract and consequently hydrolysis of dietary fats contribute to increase of the serum Low Density Lipoprotein levels. Several human dietary enzymes are involved in this hydrolysis reaction. A further reason to reduce the hydrolysis of dietary fats and the subsequent liberation of fatty acids is to prevent or to reduce an increase of body weight or event to reduce the body weight.

Also other enzymes in the gastrointestinal tract may be involved in undesirable physiological reactions. Examples of such enzymes, which are referred to as human dietary enzymes include oxidoreductases, transferases, hydrolases (e.g. lipases, proteolytic enzymes and ureases), lyases, isomerases and ligases or synthetases.

There is therefore a need to find ways to reduce the amount of liberated fatty acids in the stomach and intestinal tract for example by inhibiting or modulating the activity of human dietary enzymes.

DESCRIPTION OF RELATED ART INCLUDING INFORMATION DISCLOSED UNDER 37 CFR 1.97 AND 1.98.

WO 98/34630 describes the use of a gastrointestinal lipase inhibitor for the manufacture of oral medicaments for treating or preventing type II diabetes mellitus. A preferred gastrointestinal lipase inhibitor is tetrahydrolipstatin.

There is a desire to identify natural alternatives to tetrahydrolipostatin for the inhibition of human lipase or other human dietary enzymes. Even more desired is the identification of materials which are capable of partial inhibition of human dietary enzymes, therewith possibly reducing, but not completely blocking the liberation of fatty acids in the human tract.

Aoubala et al in The Journal of Biological Chemistry, 8, 1995 pp 3932-3937 discloses monoclonal antibodies against human pancreatic lipase. Also Bezzine et al in Biochemistry (1998), 11846-11855 describes the binding of monoclonal antibodies to human pancreatic lipase. However a problem with monoclonal antibodies is that they are expensive, difficult to prepare and are generally not stable under the conditions in the human tract.

There remains a continuing need for the development of new and improved methods for the inhibition or modulation of human dietary enzymes. In particular there is a need to develop effective gastrointestinal lipase inhibitors, which can conveniently be prepared and which are sufficiently stable under the conditions found in the human tract.

BRIEF SUMMARY OF THE INVENTION

Surprisingly it has been found that a special class of antibodies or fragments thereof namely those which are naturally free of light chains and commonly referred to as $V_HHs$ can be used for the inhibition or modulation of human dietary enzymes.

Accordingly the present invention relates to an antibody, or fragment thereof, capable of binding specifically to one or more human dietary enzymes, said antibody or fragment thereof comprising a heavy chain variable domain derived from an immunoglobulin naturally devoid of light chains, or a functional equivalent thereof.

According to a second aspect the invention relates to the use of an antibody, or fragment thereof, capable of binding specifically to one or more human dietary enzymes, said antibody or fragment thereof comprising a heavy chain variable domain derived from an immunoglobulin naturally devoid of light chains, or a functional equivalent thereof for modulating the activity of human dietary enzymes.

In a third aspect the invention relates to the use of an antibody, or fragment thereof, capable of binding specifically to one or more human dietary enzymes, said antibody or fragment thereof comprising a heavy chain variable domain derived from an immunoglobulin naturally devoid of light chains, or a functional equivalent thereof in food products, including for example nutraceutical food products and dietary supplements.

In a fourth aspect the invention relates to the use of an antibody, or fragment thereof, capable of binding specifically to one or more human dietary enzymes, said antibody or fragment thereof comprising a heavy chain variable domain derived from an immunoglobulin naturally devoid of light chains, or a functional equivalent thereof for the preparation of pharmaceutical products.

The invention will be further clarified in the following:

BRIEF DESCRIPTION OF TERMS

The term "$V_HH$" refers to the single heavy chain variable domain antibodies of the type that can be found in Camelid mammals which are naturally devoid of light chains; synthetic $V_HH$ can be construed accordingly.

As used herein, the term "antibodies" refers to immunoglobulins which may be derived from natural sources or may be synthetically produced, in whole or as antibody fragment.

An "antibody fragment" is a portion of a whole antibody which retains the ability to exhibit antigen binding activity. Functionalized antibody fragments are also embraced in this term.

The term "functionalized antibody fragment" is used for indicating an antibody or fragment thereof to which one or more functional groups, including enzymes and other binding polypeptides, are attached resulting in fusion products of such antibody fragment with another biofunctional molecule.

The term "traditional antibody" is used for an antibody which normally consists of two heavy and two light chains or fragments thereof.

The term "human dietary enzymes" is used for enzymes which may be present and are physiologically active in the gastro-intestinal tract e.g. under stomach conditions or under intestinal conditions.

BRIEF DESCRIPTION OF THE SEVERAL VIEWS OF THE DRAWING(S)

The present invention may be more fully understood with reference to the following description when read together with the accompanying drawings in which:

FIG. 1 shows the titration of serum antibodies from the llama immunised with Human Pancreatic Lipase in ELISA on enzyme recognition (A) and on inhibition of lipase activity (B);

FIG. 2 analyses the efficiency of individual $V_HH$ fragments to recognise Human Pancreatic Lipase (determined with ELISA) (2A) and to inhibit lipase activity (2B);

DETAILED DESCRIPTION OF THE INVENTION

Figure 1A:
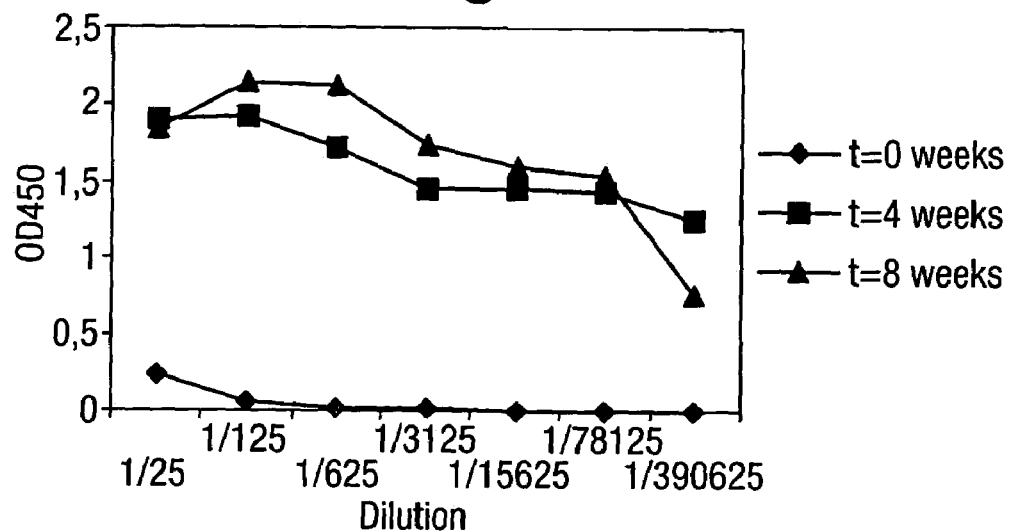

Antibodies are protein molecules belonging to a group of immunoglobulins generated by the immune system in response to an antigen. The structure of most antibody molecules is based on a unit comprising four polypeptides, two identical heavy chains and two identical light chains, which are covalently linked by disulphide bonds. Each of these chains is folded in discrete domains. The carboxy-terminal regions of both heavy and light chains are conserved in sequence and are called the constant regions, comprising one or more so-called C-domains. The amino-terminal regions of the heavy and light chains, also known as variable (V) domains, are variable in sequence and determine the specificity of the antibody. The regions in the variable domains of the light and heavy chains ($V_L$ and $V_H$ respectively) responsible for antigen binding activity are known as the hypervariable or complementarity determining regions (CDR), while the framework regions (FR) are responsible for the typical immunoglobulin fold of the V-region.

Natural antibodies generally have at least two identical antigen-binding sites defined by the association of the heavy and light chain variable regions. Generally most naturally occurring antibodies need both a $V_H$ and $V_L$ to form a complete antigen binding site and retain full immunoreactivity.

More recently, immunoglobulins capable of exhibiting the functional properties of the four-chain immunoglobulins described above but which comprise two heavy polypeptide chains and which furthermore are devoid of light polypeptide chains have been described in WO 94/04678. Methods for the preparation of such antibodies or fragments thereof on a large scale comprising the transformation of a mould or yeast with an expressible DNA sequence encoding the antibody or fragment are described in WO 94/25591.

The immunoglobulins described in WO 94/4678, which may be isolated from the serum of Camelids, do not rely upon the association of heavy and light chain variable domains for the formation of the antigen-binding site but instead the heavy polypeptide chains alone naturally form the complete antigen binding site. These immunoglobulins, hereinafter referred to as "heavy-chain immunoglobulins" (or $V_HH$) are thus quite distinct from the heavy chains obtained by the degradation of common (four-chain) immunoglobulins or by direct cloning which thereby contain only a part of the antigen-binding site and require a light chain partner for the formation of a complete antigen binding site in order to obtain optimal antigen-binding characteristics.

Surprisingly it has been found that $V_HH$'S, are capable of inhibiting human dietary enzymes, in particular enzymes involved in the hydrolysis of dietary fats, and thereby educe the absorption of free fatty acids effectively.

It has been found that $V_HH$'s can be used for the inhibition of several human dietary enzymes. Examples of human dietary enzymes that can be inhibited are oxidoreductases, transferases, hydrolases (e.g. lipases, proteolytic enzymes and ureases), lyases, isomerases and ligases or synthetases.

In a preferred embodiment of the invention $V_HH$'s are used for the inhibition of human enzymes involved in the hydrolysis of dietary fats, examples of these enzymes are Human Pancreatic Lipase and Human Gastric Lipase.

Human Pancreatic Lipase (HPL) is the major lipase responsible for lipid conversion in adults, accounting for 48.5% of the hydrolysis of the triacylglyceride. The enzyme is active at neutral pH in the small intestine, where it catalyses the hydrolysis of fatty acids in the sn-1 and sn-3 position of triacylglycerides. The enzyme requires a cofactor called colipase for lipolytic action on duodenal fats. The structure of HPL consists of an amino-terminal domain (residues 1 through 336) and a carboxy-terminal domain (residues 337 through 448) that is involved in binding colipase.

Human Gastric Lipase (HGL) belongs to the family of the acid lipase family, which refers to its stability and activity in the highly acidic environment of the stomach. HGL is responsible for the hydrolysis of 17.5% of the meal triacylglyceride. The crystal structure of the enzyme, which contains 379 amino acid residues, reveals the presence of a core domain typical for the alpha/beta hydrolase family and a "cap" domain, similar to what has been found in Serine carboxypeptidases.

A preferred embodiment of the present invention involves the partial inhibition of human dietary enzymes using $V_HH$'s. Preferably the enzymes, for example the human lipases, are only partially inhibited to ensure that no deficiencies of important ingredients will occur. Preferably the level of inhibition, measured in accordance to FIG. 3 is between 2 to 90%, more preferred 3-30%, most preferred 5-20%.

For the purpose of the invention antibodies can be used in their entirety (e.g. in a form which is equal to or closely resembles the natural form in the Camelid source). Alternatively, however fragments of these antibodies e.g. $V_HH$'s may be used. If fragments are used then it is preferred that these fragments comprise one or more sequences which are equal to or closely resemble the CDR regions in the natural $V_HH$'s. Particularly preferably these fragments comprise a sequence which is equal to or closely resembles the CDR3 region of a natural $V_HH$.

In a particular preferred embodiment the $V_HH$'s (including either entire $V_HH$'s or fragments thereof) according to the present invention are characterised by a CDR3 selected from the following classes:

| | |
|---|---|
| (I) | ARSLX$_1$X$_2$TPTSYDY |
| | (SEQ ID NO: 1; |
| | SEQ ID NO: 2; |
| | SEQ ID NO: 3; |
| | SEQ ID NO: 4) |
| (II) | RGGLTQYSEHDY |
| | (SEQ ID NO: 5) |
| (III) | TGAEGHY |
| | (SEQ ID NO: 6) |
| (IV) | TDMGRYGTSEW |
| | (SEQ ID NO: 7) |

Wherein $X_1$ is V or E and $X_2$ is Q or L.

Preferred examples of $V_HH$'s of the first class are HGL#1 (SEQ ID NO: 27) and HGL#16(SEQ ID NO: 34). Preferred examples of $V_HH$'s of the second class are HGL#4 (SEQ ID NO: 28) and HGL#10 (SEQ ID NO: 31). Preferred examples of $V_HH$'s of the third class are HGL#8 (SEQ ID NO: 29) and HGL#9 (SEQ ID NO: 30). A preferred example of $V_HH$'s of the fourth class is HGL#11 (SEQ ID NO: 32).

In another particular preferred embodiment the $V_HH$'s according to the present invention are chacterised by a CDR3 selected from the following classes:

| | |
|---|---|
| (a) | DVRPYRTSRYLEX$_3$ |
| | (SEQ ID NO: 8; |
| | SEQ ID NO: 9; |
| | SEQ ID NO: 10) |
| (b) | QVRVRFSSDYTNY |
| | (SEQ ID NO: 11) |
| (c) | LIRRKFTSEYNEY |
| | (SEQ ID NO: 12) |
| (d) | LITRWDKSVNDY |
| | (SEQ ID NO: 13) |
| (e) | RRSNYDRSWGDY |
| | (SEQ ID NO: 14) |
| (f) | LISSYDGSWNDY |
| | (SEQ ID NO: 15) |
| (g) | HITPAGSSNYVYGY |
| | (SEQ ID NO: 16) |
| (h) | DIRKRFTSGYSHY |
| | (SEQ ID NO: 17) |

Whereby $X_3$ is V or L or I

An example of a $V_HH$ of class (a) is HPL#12(SEQ ID NO: 19), HPL#14(SEQ ID NO: 21), and HPL#30(SEQ ID NO: 26), An example of a $V_HH$ of class (b) is HPL#19(SEQ ID NO: 24), An example of a $V_HH$ of class (c) is HPL#18 (SEQ ID NO: 23), An example of a $V_HH$ of class (d) is HPL#13 (SEQ ID NO: 20), An example of a $V_HH$ of class (e) is HPL#11 (SEQ ID NO: 18), An example of a $V_HH$ of class (f) is HPL#22(SEQ ID NO: 25), An example of a $V_HH$ of class (g) is HPL#15(SEQ ID NO: 22), An example of a $V_HH$ of class (h) is HPL#17.

$V_HH$'s in accordance with the present invention can be used for the inhibition of the activity of human dietary enzymes. Surprisingly it has been found that the $V_HH$'s are often more stable than traditional antibodies under conditions similar to those in the gastric intestinal tract. In particular preferred $V_HH$'s in accordance with the invention have a stability (as measured in example 4.3) of at least 75% after 1 hour.

$V_HH$'s in accordance with the present invention can be administered to human beings in any desirable form. In a first preferred embodiment of the invention the $V_HH$'s can be used in pharmaceutical compositions. These compositions normally comprise in addition to the $V_HH$'s a suitable carrier material. For example the $V_HH$'s can be incorporated into medicines for oral use such as tablets, capsules, medicinal liquors, powders, but other application forms e.g. as an injection, topical applications etc may equally be suitable.

In a second preferred embodiment of the inventions the $V_HH$'s can be used in food products. Examples of suitable food products are margarines and other bread spreads, dressings, beverages including fruit juices and tea and coffee, bakery products such as cookies, biscuits, bread, pizza etc, sauces including hot or cold sauces, frozen confectionery materials e.g. water-ice or ice-cream, dairy products e.g. desserts, yoghurt, cheese etc, cereal products, for example breakfast cereals, sweets such as pastilles, lollypops, bars, chocolate etc.

Typically a suitable intake per meal of antibodies could be such that the molar ratio of antibody to the relevant dietary enzyme is between 10:1 and 1:10. It is well within the ability of the skilled person to adapt the concentration of antibodies in the product such that these amounts are consumed.

The invention is applicable to the use of any immunoglobulin variable domain, which forms a complete antigen binding site. The immunoglobulin may be derived from natural sources or synthetically produced. Preferably, the invention relates to the use of heavy chain variable domains derived from an immunoglobulin devoid of light chains, most suitably from an immunoglobulin naturally devoid of light chains such as are obtainable from lymphoid cells, especially peripheral blood lymphocytes, bone marrow cells or spleen cells derived from Camelids as described in WO 94/04678 (Casterman et al).

It will be appreciated that heavy chain variable domains derived from other immunoglobulins modified to enable them to function as monovalent binding domains in the same way as the heavy chain variable domains derived from Camelids may also suitably be used according to the invention. For the purpose of this invention these molecules are referred to as functional equivalents.

A major advantage of the use of single domain binding units, which are heavy chain variable domains derived from Camelids, is their unusual stability against extreme pH, degradation by proteases, high concentrations of salts and high temperatures, which makes these fragments suitable for application in food products and to be effective in the Gastro-intestinal tract. Another benefit of single domain binding units is that these molecules can readily and conveniently be produced economically on a large scale, for example using a transformed lower eukaryotic host as described in WO 94/25591 (Unilever). This describes a production system that delivers high amounts of secreted antibody fragments with a low degree of impurities present in the secreted fraction, thereby enabling simple down stream processing procedures for purification.

The invention also provides host cells and expression vectors enabling high levels of production and secretion of the binding proteins.

Heavy chain variable domains derived from an immunoglobulin naturally devoid of light chains having a determined antigen specificity may conveniently be obtained by screening expression libraries of cloned fragments of genes encoding Camelid immunoglobulins generated using conventional techniques, as described, for example, in EP-A-0584421 and Example 1. Preferred methods to enrich for binding domains recognising the human dietary enzyme, thereby limiting the numbers of clones, which have to be screened for the identification of inhibiting fragments, are yeast display (WO 94/01567 from Unilever) or phage display.

Enzyme inhibiting antigen binding proteins may be prepared by transforming a host by incorporating a gene encoding the polypeptide as set forth above and expressing said gene in said host.

Suitably the host or hosts may be selected from prokaryotic bacteria, such as Gram-negative bacteria, for example *Escherichia coli*, and Gram-positive bacteria, for example *Bacillus subtilis* and in particular lactic acid bacteria, lower eukaryotes such as yeasts, for example belonging to the genera *Saccharomyces, Kluyveromyces, Hansenula* or *Pichia*, or moulds such as those belonging to the genera *Aspergillus* or *Trichoderma*.

Preferred hosts for use in connection with the present invention are the lower eukaryotic moulds and yeasts.

Techniques for synthesising genes, incorporating them into hosts and expressing genes in hosts are well known in the art and the skilled person would readily be able to put the invention into effect using common general knowledge.

Proteins for use according to the invention may be recovered and purified using conventional techniques such as affinity chromatography, ion exchange chromatography or gel filtration chromatography.

The binding activity of the binding proteins prepared according to the invention may conveniently be measured by standard techniques known in the art such as enzyme-linked immunoadsorbant assay (ELISA), radioimmune assay (RIA) or with biosensors.

The following examples are provided by way of illustration only. Techniques used for the manipulation and analysis of nucleic acid materials were performed as described in (Sambrook et al., 1990), unless otherwise indicated.

EXAMPLES

Example 1

Induction of a Humoral Immune Response in Llama

Human Pancreatic Lipase (HPL) was purified as described by De Caro, A., Figarella, C., Amic, J., Michel, R. & Guy, O. (1977). *Biochim. Biophys. Acta* 490(2), 411-419.

A llama was immunised with an HPL in oil emulsion obtained by mixing 2 ml antigen in water and 3 ml Specol, (Bokhout, B. A., Van Gaalen, C. & Van der Heijden, P. J. (1981) *Vet. Immunol. Immunopath.* 2, 491-500.

Figure 1B:
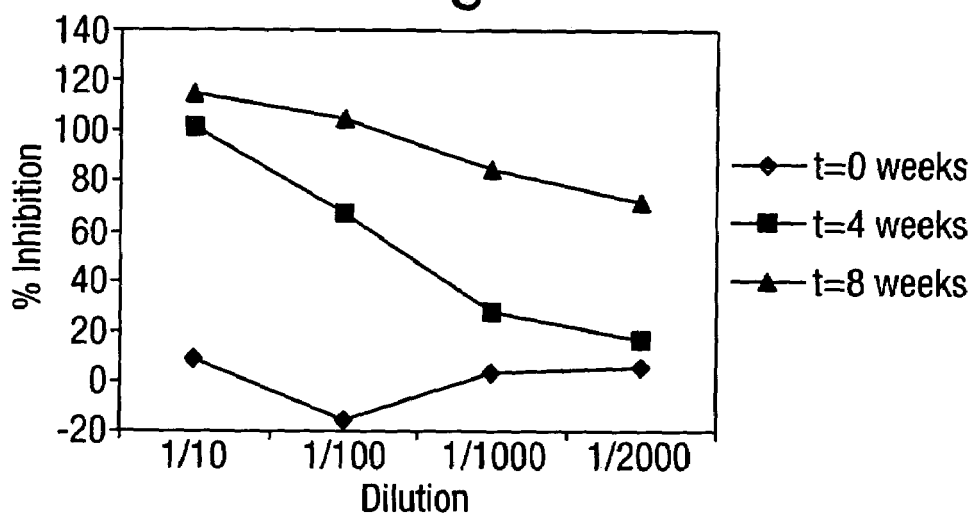

Per immunisation 4 times 1.25 ml water in oil emulsion was injected said 1.25 ml containing 200 µg enzyme. Each immunisation involved 4 injections two of the injections were subcutaneous, the other two inter-muscular. The second immunisation was performed four weeks after the first injection, the third immunisation 8 weeks after the first injection and the fourth immunisation 12 weeks after the first injection. The immune response was monitored by titration of serum samples in two different assays. In the first assay the serum antibodies recognising HPL were quantified in ELISA (FIG. 1A), and in the other one the titre of inhibiting antibodies was determined in an enzyme activity assay (FIG. 1B).

For ELISA in vitro biotinylated HPL (prepared as described in paragraph 2.2) was immobilised indirectly via streptavidin. Streptavidin was coated at 5 µg/ml in Phosphate Buffered Saline (PBS) during two hours at room temperature in MAXISORB plates (NUNC). The coat solution was removed and, after washing with 0.05 vol % Tween-20 in PBS (PBST), the wells were blocked during 30 minutes at room temperature with a 4 wt % skimmed milk solution made in PBS. Biotinylated HPL was captured by the coated streptavidin during 16 hours at 4° C. from a solution with a concentration of 2.5 µg/ml enzyme in PBST, followed by washing of the plate with PBTS to remove free biotinylated HPL.

Serum samples were tested in serial dilutions (in 2% skimmed milk solution in PBST). Subsequently the bound llama antibodies were detected with polyclonal rabbit-anti-llama antiserum (obtained via immunising rabbits with llama immunoglobulins purified via Protein A and Protein G columns (Hamers-Casterman, C., Atarhouch, T., Muyldermans, S., Robinson, G., Hamers, C., Songa, E. B., Bendahman, N. & Hamers, R. (1993). Nature 363(6428), 446-448.) and swine-anti-rabbit immunoglobulins (DAKO) conjugated to horse radish peroxidase. Finally the peroxidase enzyme-activity was determined with tetramethyl-benzidine and ureaperoxide as substrates and the optical density was measured at 450 nm after termination of the reaction by the addition of $H_2SO_4$.

The titre of inhibiting antibodies was determined in the LIPASE-PS assay (Sigma Diagnostics), in which the enzymatic hydrolysis of 1,2-diglyceride into 2-monoglyceride and fatty acid can be measured kinetically in a spectrophotometer at a wavelength of 550 nm. For this assay 5 µl (diluted) serum was mixed with 10 µl distilled water and 5 µl HPL (approximately 250 lipase units/ml. From this mixture 5 µl was added to 150 µl substrate solution (LIPASE-PS Substrate Reagent) using the wells of a microtiter plate as reaction vessels. After incubating the plate for 8 minutes at 37° C., Activator solution (50 µl/well) was added and colour development was measured kinetically during a period of 10 minutes at 550 nm and 37° C., whereby a change in colour intensity implied enzymatic activity.

Example 2

Cloning, Selection and Screening of Clones Producing Llama $V_HH$ Fragments Inhibiting Human Pancreatic Lipase 2.1 Isolation of $V_HH$ fragments against Human Pancreatic Lipase.

Llama RNA was isolated from its lymphocytes using a blood sample taken 8 weeks after the first immunisation. At that point in time the llama had the highest titre of HPL recognising antibodies as measured in ELISA.

A blood sample of about 150 ml was taken and an enriched lymphocyte population was obtained via centrifugation on a Ficoll Paque (Pharmacia) discontinuous gradient. From these cells total RNA was isolated by guanidium thiocyanate extraction according to Chomczynski, P. & Sacchi, N. (1987). Anal. Biochem. 162(1), 156-159. After first strand cDNA synthesis using MMLV-RT (Gibco-BRL) and random oligonucleotide primers (Pharmacia), DNA fragments encoding $V_HH$ and part of the long or short hinge region were amplified by PCR using three specific primers as described in example II.2.1 of WO99/46300.

Figure 4:
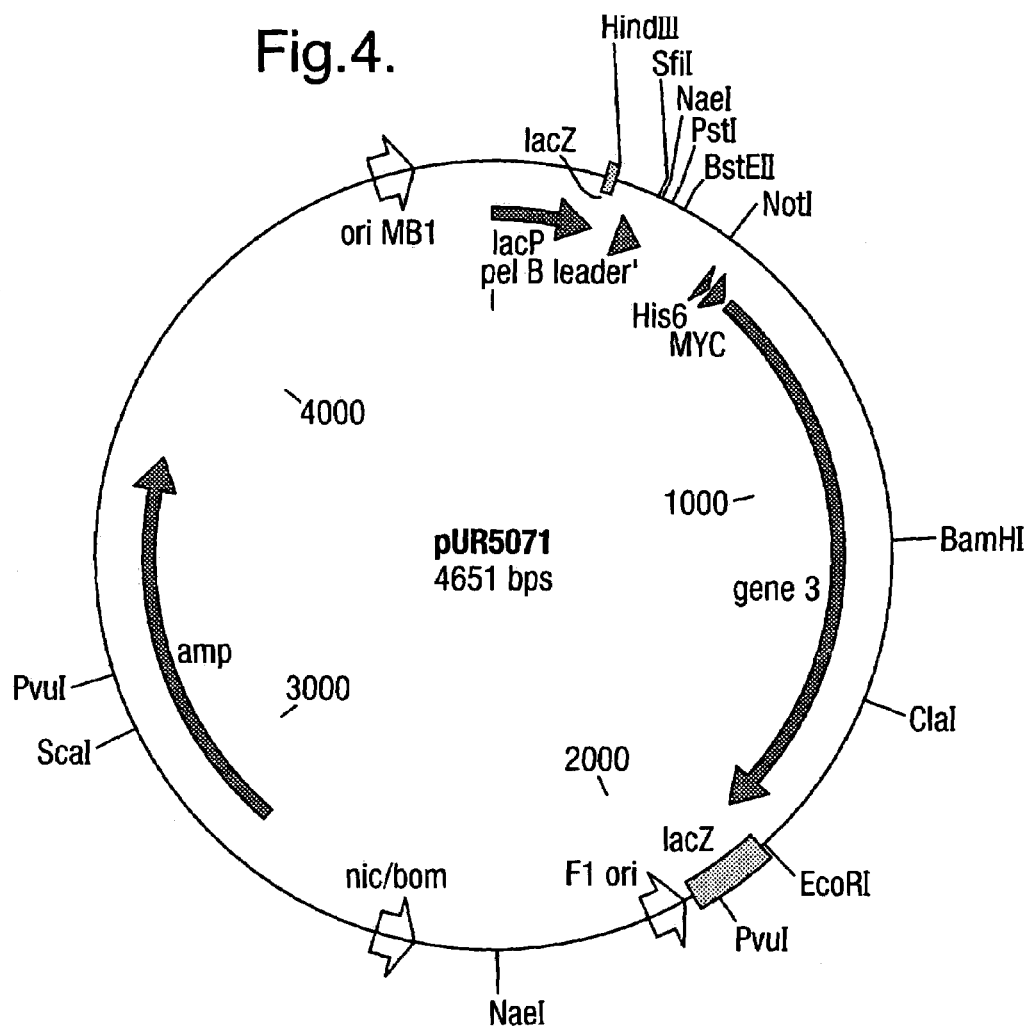
FIG. 4 is a restriction map of phagemid pUR5071.

The DNA-fragments generated by PCR were digested with PstI (coinciding with codon 4 and 5 of the $V_HH$ domain, encoding the amino acids L-Q) and NotI (introduced at the 5' end of the hinge specific oligonucleotide primers, coinciding with the amino acid sequence A-A-A). The digested PCR products were cloned in the phagemid vector pUR5071 (FIG. 4) as gene-fragments encoding the $V_HH$ domain including the hinge region fused to the gene III protein of the *E. coli* bacteriophage M13. A first display library with $1.5 \times 10^7$ clones containing the short hinge derived $V_HH$ fragments and a second library of $6.2 \times 10^7$ clones with long hinge derived $V_HH$, was constructed in phagemid vector pUR5071.

2.2 Enrichment of HPL Binding $V_HH$ Domains Via Phage Display Methodology.

Phage particles exposing $V_HH$ fragments were prepared by infection of *E. coli* cells harbouring the phagemid with helperphage VCS-M13 according to Marks, J. D et. al (1991) *J. Mol. Biol.* 222, 581-597.

Free $V_HH$ fragments were removed by precipitation of phage from the culture supernatant with PEG6000, thereby avoiding a disturbing competition between phage bound and free $V_HH$ fragments. "In solution" capture of *E. coli* phage exposing HPL specific antibody fragments was performed with in vitro biotinylated lipase (EZ link NHS-biotin) covalently coupled to free $NH_2$-groups of the lipase according to the instructions of the supplier; the molar ratio between biotin and lipase was 15 to 1). For selection 15 nM and 40 nM Human Pancreatic Lipase was used in round one and 0.6 nM and 3 nM in round two. The carboxy terminal domain was prepared by proteolysis with chymotrypsin and purified with reversed phase HPLC. Lipase was biotinylated and used for selection of the immune library (combined short hinge and long hinge) at 15 and 70 nM during round one and at 1 and 3 and 15 nM during round two. During the binding phase of the selection "application conditions" (inclusion of 5.3 mM cholic acid and 36 mM deoxycholate) were used. Phage particles bound via their displayed antibody fragments to the biotinylated lipase or the carboxy terminal domain peptide were pulled out of the solution with streptavidin coated magnetic beads (Dynal) (see (Hawkins, T, DNA Seq. 1992; 3(2) 65-9). After washing, phage was eluted with triethylamine.

Individual *E. coli* clones obtained after two rounds of selection were grown in wells of microtiter plates, and the production of $V_HH$ fragments was induced by the addition of 0.1 mM isopropyl-β-D-thiogalactopyranoside. After 16 hours of growth, the culture supernatant of the clones was analysed in ELISA for the presence of $V_HH$ fragments, which specifically bind to indirectly immobilised biotinylated HPL, using a streptavidin coated plate as a negative control. Bound $V_HH$ fragments were detected with rabbit anti-llama $V_HH$ polyclonal antibodies followed by incubation with goat anti-rabbit polyclonal antibodies conjugated to horse radish peroxidase (BIORAD), or with mouse monoclonal anti-myc antibody ATCC myc 1-9E 10-2 followed by incubation with polyclonal rabbit anti-mouse conjugated to horse radish peroxidase (DAKO). The myc-tag is encoded in the phage display vector, which results in the addition of this peptide sequence to the carboxy terminus of the $V_HH$ fragments.

2.3 Development of a High-Throughput Screening Assay for the Identification of Lipase Inhibiting $V_HH$ Fragments.

The lipase inhibiting capacity of the $V_HH$ fragments was demonstrated in an enzyme activity assay (Sigma). Different anti-HPL clones were identified by their characteristic HinFI fingerprint pattern (Marks et al., as above), for which the $V_HH$ encoding insert was amplified with the M13REV- and the gene III-primer. The resulting PCR-product was digested with the restriction enzyme HinFI, whose recognition site frequently occurs within antibody genes. The representative clones were grown on 5 ml scale and the cells were harvested after a relative short induction time of 3.5 hours at 37° C. An osmotic shock was given by resuspending and incubating the pelleted cells in 0.5 ml of ice-cold PBS during two to sixteen hours at 4° C. Spheroplasts were removed by centrifugation and the supernatant, containing the periplasmic proteins, was tested in ELISA in serial dilutions for binding to biotinylated HPL and in the lipase enzyme assay for their capacity to inhibit the enzyme.

Selection with biotinylated lipase or its carboxy terminal domain resulted in the isolation of clones, which produce inhibiting $V_HH$ fragments.

2.4 Sequences of HPL Inhibiting $V_HH$ Fragments.

By using biotinylated HPL enzyme 190 inhibiting $V_HH$ fragments were selected, 8 of these were sequenced, these fragments are coded HPL#11(SEQ ID NO:18), HPL#12 (SEQ ID NO: 19), HPL#13(SEQ ID NO: 20), HPL#15(SEQ ID NO: 22), HPL#18(SEQ ID NO: 23), and HPL#19(SEQ ID NO: 24).

By using the carboxy terminal domain of HPL 95 lipase inhibiting $V_HH$ fragment were selected, 6 were sequenced, resulting in one new class represented by HPL#22 (SEQ ID NO: 25).

With respect to the length of CDR3, which is the most important region for binding to the antigen, the antibodies can be grouped in three classes, as is shown in the following amino acid sequences, wherein the respective CDR regions are indicated in bold CDR1 being the first bold strand etc. HPL#12 (SEQ ID NO: 19), HPL#18 (SEQ ID NO: 23) and HPL#19 (SEQ ID NO: 24) are characterised by a CDR3 region having a length of 13 amino acids, HPL#11 SEQ ID NO: 18), HPL#13 (SEQ ID NO: 20) and HPL#22 (SEQ ID NO: 25) are characterised by a CDR3 region of 12 amino acids and HPL#15 (SEQ ID NO: 22) is characterised by a CDR3 region of 14 amino acids.

```
HPL#11 (SEQ ID NO: 18)
QVQLQDSGGGLVQAGGSLRLSCAASGSIFS SDLMG      49

WYRQAPGKEREAVA RITRGGTTSYADSVK            97

GRFTISRDNAKNTMYLQMNSLKPEDTAVYYCNA        129

RRSN--YDRSWGDY WGQGTQVTVSS  AHHSEDPSS

HPL#12 (SEQ ID NO: 19)
QVQLQESGGGLVQAGGSLRLSCAASGSIGS IHTMG      49

WYRQTPGKERDVVA TIQDGGSTNYADSVK            97

GRFTISRDNTLNTVYLQMNDLKPEDTAVYYCNA        130

DVRP-YRTSRYLEV WGQGTLVTVSS  EPKTPKPQP
```

-continued

HPL#13 (SEQ ID NO: 20)
QVQLQESGGGLVQAGGSLRLSCAASGTILS IIYMD  49

WYRQTPGKQRELVG RITAGGSTNYADSAK  97

GRFTISKDNAKNTVYLQMNSLKPEDTAVYYCNA

LITR--WDKSVNDY WGQGTQVTVSS EPKTPKPQP  129

HPL#14 (SEQ ID NO: 21)
QVQLQESGGGLVQAGGSLRLSCAASGSIGS IHTMG

WYRQTPGTERDVVA TIQDGGSTNYADSVK

GRFTISRDNILNTVYLQMNSLKPEDTAVYHCNA

DVRPYRTSRYLEL WGQGTLVTVSS EPKTPKPQP

HPL#15 (SEQ ID NO: 22)
QVQLQESGGGLVQAGGSLRLSCAASGSISS INVMG  49

WFRQAPGKQRELVA SITSGGSTNYADSLK  97

GRFTISRDNAKNAVYLQMNNLKPEDTAVYYCNA

HITPAGSSNYVYGY WGHGTKVTVSS EPKTPKPQP  131

HPL#18 (SEQ ID NO: 23)
QVQLQDSGGGLVQAGGSLRLSCAASGTIGD IYTMA  49

WHRQAPGKERELVA SATESGSPNYADPVK  97

GRFTISRDNGKLTVYLQMNSLKPEDTAVYYCNA

LIRR-KFTSEYNEY WGQGTQVTVSS EPKTPKPQP  130

HPL#19 (SEQ ID NO: 24)
QVQLQDSGGGLVQTGGSLRLSCAASGPIGD VYLMG  49

WYRQAPGKQREMVA SITATGPPNYTDSVK  97

GRFTISRDNDKNTEYLQMNNLKPEDTAVYYCNA

QVRV-RFSSDYTNY WGQGTQVTVSS EPKTPKPQP  130

HPL#22 (SEQ ID NO: 25)
QVQLQESGGGLVQAGGSLRLSCAASGSIRS ISIMT  49

WYRQAPGKERELVA RMSSDGTTSYTDSMK  97

GRFTISRDNAKNTVYLHMNNLKPEDTAVYYCKA

LISS--YDGSWNDY GGQGTQVTVSS EPKTPKPQP  129

HPL#30 (SEQ ID NO: 26)
QVQLQDSGGGLVQAGGSLRLSCAASGSIGD IHTMG

WYRQTPGKQRDVV ATIQSGGSTNYADSVK

GRFTISRDNTLNTVYLQMNDLKPEDTGVYYWNA

DVRPYRTSRYLEI WGQGTLVTVFL EPKTPKPQP.

Example 3

The Efficacy of $V_HH$ Fragments to Inhibit Human Pancreatic Lipase 3.1 Recloning in Episomal Plasmid System for Production of Anti-HPL $V_HH$ Fragments in Saccharomyces cerevisiae The $V_HH$ encoding sequences of clones HPL#11(SEQ ID NO: 18), HPL#13(SEQ ID NO: 20), HPL#15(SEQ ID NO: 22), HPL#17, HPL#18 (SEQ ID NO: 23) and HPL#19 (SEQ ID NO: 24) were digested with PstI and BstEII from the E. coli phagemid vectors pUR5084, pUR5082, pUR5095, pUR5080, pUR5086 and pUR5087 respectively, and cloned in the episomal S. cerevisiae plasmid pUR4547 (deposited at the CBS, Baarn, The Netherlands as CBS100012) for the secretion of $V_HH$ fragments, thereby obtaining pUR5091, pUR5090, pUR1403, pUR5088, pUR5092 and pUR5093 respectively. Secretion of $V_HH$ fragments with carboxy terminal tag-sequences was accomplished by cloning in plasmid pUR4585, which is identical to plasmid pUR4547 except encoding the myc-tag for detection with monoclonal antibody myc 1-9E10.2 (ATCC) and the hexahistidine tail for purification with IMAC. Plasmid constructs pUR5099, pUR5098, pUR5097, pUR5096, pUR5263 and pUR5264 were made encoding the tagged $V_HH$ fragments of HPL#11 (SEQ ID NO: 18), HPL#13(SEQ ID NO: 20), HPL#15(SEQ ID NO: 22), HPL#17, HPL#18 (SEQ ID NO: 23) and HPL#19 (SEQ ID NO: 24) respectively.

Both parental plasmids pUR4547 and pUR4585 contain the GAL7 promoter for inducible expression of the $V_HH$ gene product, the selectable markers bla (β-lactamase) to discriminate transformants in E. coli by resistance to the antibioticum ampicillin and Leu2d (β-isopropylmalate dehydrogenase) for selection of transformed S. cerevisiae, and an E. coli origin of replication. Secretion is accomplished by fusing the SUC2 leader sequence to the amino terminus of the $V_HH$ product according to Harmsen, M. M. et al (1993) Gene 125, 115-123.

Clones HPL#14 (SEQ ID NO: 21) and HPL#16, which lack the BstEII-site, were cloned as PstI/NotI-fragments (including their hinge region) in secretion plasmid pUR1400, which is identical to pUR4585 except with the additional NotI cloning site situated between the BstEII-site and the myc-/hexahistidine-tags. In this way plasmid constructs pUR5265 and pUR5266 were obtained containing the $V_HH$ genes of clones HPL#14 (SEQ ID NO: 21) and HPL#16 respectively.

Transformants in E. coli containing the S. cerevisiae shuttle constructs with the $V_HH$ genes were identified by PCR screening using primers M13REV and M13U for amplification of the $V_HH$ encoding insert and by restriction enzyme analysis on plasmid DNA. Plasmid DNA purified with the Quick-prep kit (Qiagen) was used for transformation of S. cerevisiae strain VWK18gal1::URA3, ura3, leu2 by the lithium acetate procedure as described by Gietz, R. D et al (1995) Yeast 11(4), 355-360.

Two clones from each construct were grown for 24 hours at 30° C. in YNB medium (0.67% Yeast Nitrogen without amino acids (Difio)) containing 2% glucose. For $V_HH$ gene expression both pre-cultures were diluted 1/10 in 1 ml of YPD medium (1% yeast extract, 2% peptone, 2% glucose, 2% galactose) for induction of the GAL7 promoter and grown during 48 hours at 30° C. using 8 wells culture plates for cultivation. The $V_HH$ production in the medium fraction of these clones was examined by analysis on a Coomassie blue stained polyacrylamide gel. Their functional characteristics were confirmed in ELISA on indirectly immobilised biotinylated HPL and in the lipase enzyme activity assay.

3.2 Purification and Characterisation of $V_HH$ Fragments Produced by S. cerevisiae.

After confirming the binding and inhibitory characteristics observed before with the E. coli produced $V_HH$ fragments, the S. cerevisiae transformants were induced in 250 ml shake flasks using 30 ml of culture medium as described in section 3.1. Following 48 hours of induction, the medium fraction was separated from the cells by centrifugation. For purification via immobilised metal affinity chromatography (IMAC) 12 ml of each medium fraction was adjusted to 50 mM NaH$_2$PO$_4$ (pH 8.0), 10 mM Tris-HCl (pH 8.0) and 100 mM NaCl and added to 1 ml of TALON column material (CLONTECH). The hexahistidine tagged $V_HH$ fragments were bound to the immobilised metal ions in a batchwise fashion by rotating the column material head-over-head during 30 minutes; washing of the column material with sonication buffer and elution with 100 mM imidazol (Sigma) was performed according to the instructions of the supplier (CLONTECH). After removal of imidazol by dialysis against PBS, the amount of purified $V_HH$ was determined by measuring the optical density at 280 nm using the calculated molar extinction coefficient. Analysis on a Coommassie stained protein gel confirmed the purity and the measured amount of $V_HH$. Between 100 and 500 μg antibody fragment was purified from 12 ml of culture.

Figure 2A:
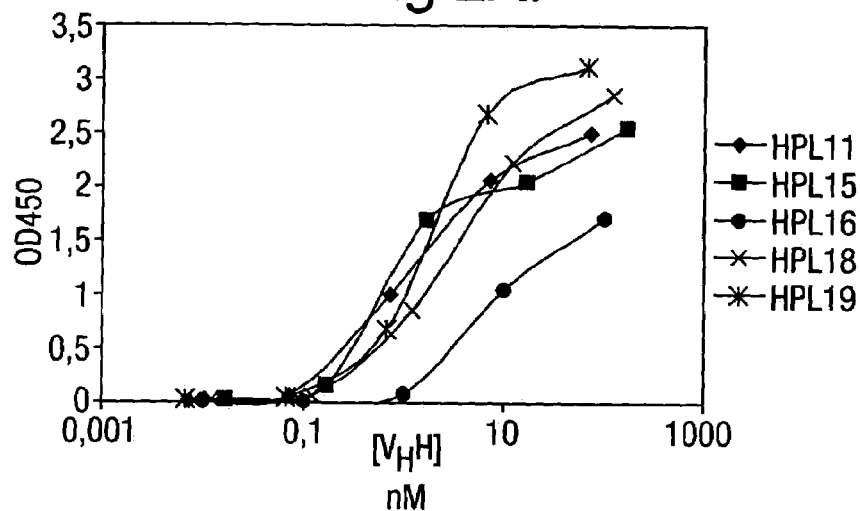
Figure 2B:
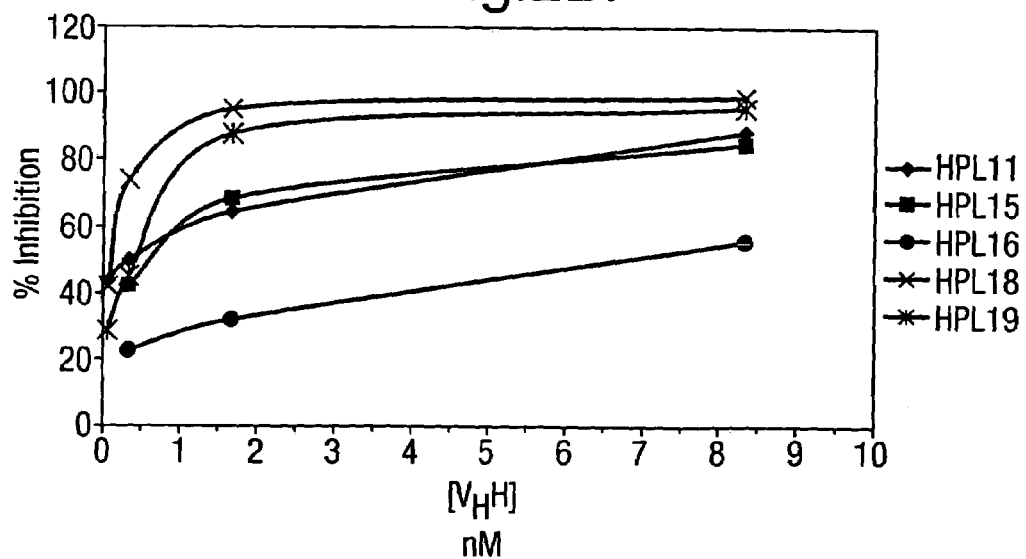

The results of the ELISA measurements are given in FIG. 2A.

3.3 Measurement of Inhibition in Intestinal Juices.

Yeast comprising pUR5099, pUR5097, pUR5263 and pUR5264 encoding the $V_HH$ domains of HPL#11(SEQ ID NO: 18), HPL#15(SEQ ID NO: 22), HPL#18 (SEQ ID NO: 23) and HPL#19 (SEQ ID NO: 24) respectively were cultivated and induced in one liter of YPD medium. The cells were removed by centrifugation and the medium fraction containing the antibody fragment was concentrated five-fold with a dialysis unit (Hemophan fiber dialyzer GFSplus 12, Gambro, Breda). HPL#11(SEQ ID NO: 18), HPL#15 (SEQ ID NO: 22) and HPL#18 (SEQ ID NO: 23) were purified by affinity chromatography on protein A sepharose (Pharmacia).

HPL#19(SEQ ID NO: 24), which did not bind to protein A, was purified with IMAC, yielding 3.7 mg $V_HH$ per liter of culture. After dialysis against PBS, the factions can be used for inhibition experiments in intestinal juice.

Example 4

Isolation of Llama $V_HH$ Fragments Capable to Inhibit Human Gastric Lipase 4.1 Isolation and Production of Inhibiting $V_HH$ Fragments Against Human Gastric Lipase.

Figure 3A:
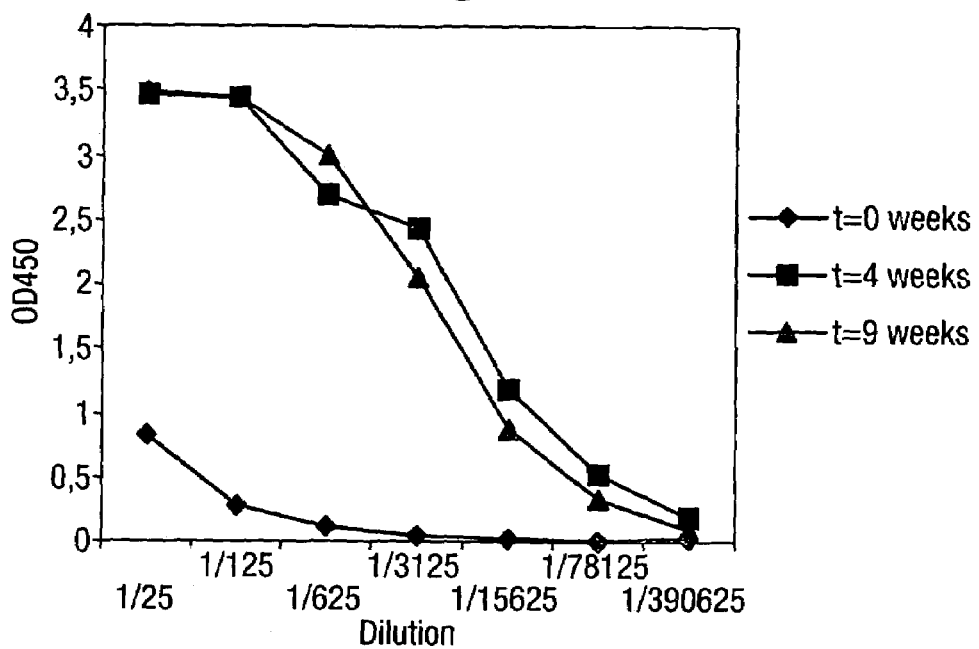
FIG. 3 shows the titration of serum antibodies of the llama immunised with Human Gastric Lipase on enzyme recognition (3A) and on lipase inhibition (3B).

A male llama was immunised with Human Gastric Lipase purified as described in Moreau, H et al (1992) *J. Mol. Biol.* 225(1), 147-153 according to the procedure indicated above and the titration of blood samples was performed on biotinylated enzyme in ELISA as described in example 1 (FIG. 3A).

Figure 3B:
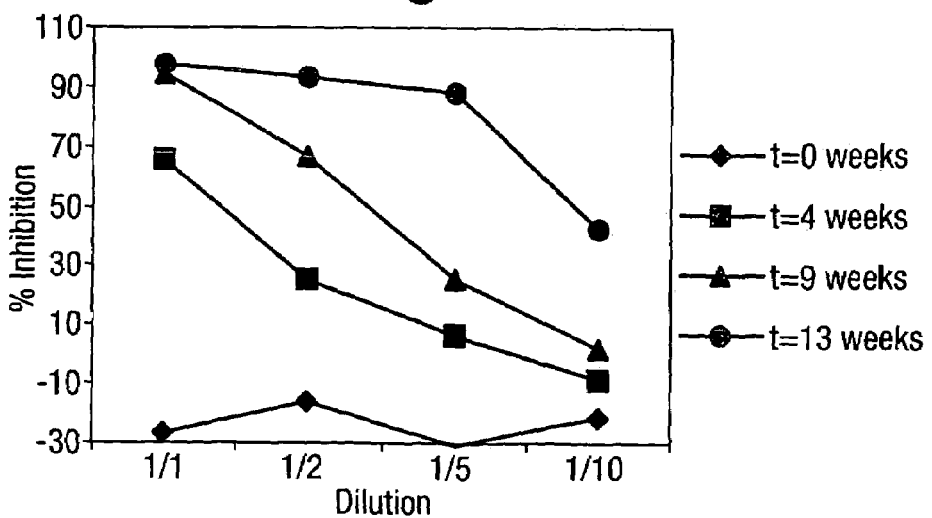

The titre of inhibiting antibodies was determined in an enzyme assay, in which 1,2-0-dilauryl-rac-glycero-3-glutaric acid-resorufin ester (DGGR, Boehringer Mannheim) was used as chromogenic substrate. For the assay 5 μl HGL solution (0.1 mg/ml) was pre-incubated with 10 μl of (diluted) serum sample in the well of a microtiter plate. The reaction was started by the addition of 165 μl of buffer containing 100 mM MES pH6.0 and 0.6 M NaCl and 20 μl DGGR solution (1 mg/ml in dioxane/Thesit-solution (1:1)). The kinetics of the enzymatic conversion was measured at 572 nm during a period of 30 minutes at 37° C. with a Spectramax spectrophotometer. With this assay the titre of enzyme inhibiting antibodies was determined in serum samples taken after different time intervals (FIG. 3B).

RNA was isolated from the lymphocytes of a blood sample taken 9 weeks after the start of the immunisation. Random primed cDNA was prepared and used for the amplification of short hinge and long hinge derived $V_HH$ fragments, which were cloned in the phagemid vector pUR5071. A short hinge derived library was constructed, which contains $5.4 \times 10^7$ clones and a long hinge derived library with $4.5 \times 10^7$ clones.

Selections were performed with 20 and 60 nM of biotinylated Human Gastric Lipase at the first round and subsequently with 1 or 6 nM lipase during the second round according to the method described in paragraph 2.2. During round one physiological conditions (PBS) were used, while at round two the conditions of the stomach were imitated by lowering the pH to 4.5 with 25 mM sodium acetate buffer and inclusion of proteases pepsin. In this way acid and protease resistant antibody fragments were retrieved from the library.

Culture supernatants from individual clones grown and induced in microtiter plates were analysed in ELISA on indirectly immobilised HGL and in the enzyme activity assay. Approximately 30 to 60% of the enzyme recognising antibody fragments showed to inhibit the enzyme.

Sequences of 8 gene segments are given below, whereby the CDR regions are indicated in bold. The $V_HH$ encoding gene segments could be classified into four groups according to the length of their CDR3 (see below). The four groups are: HGL#1 (SEQ ID NO: 27) and HGL#16(SEQ ID NO: 34); HGL#4 (SEQ ID NO: 28) and HGL#10(SEQ ID NO: 31); HGL#8(SEQ ID NO: 29), HGL#9 (SEQ ID NO: 30) and HGL#15(SEQ ID NO: 33); and HGL#11(SEQ ID NO: 32).

```
HGL#1 (SEQ ID NO: 27)
QVQLQESGGGLVQAGGSLRLSCAASGFDFR YNTMA      49

WYRQAPGKQRELVA TIASTYRTSYADSVK GRFTI      97

SRDNARGTVYLQMNSLKPEDTAVYYCAA

ARSLVQTPTSYDY WGQGTQVTVSS AHHSEDPSS       130

HGL#4 (SEQ ID NO: 28)
QVQLQESGGGLVQAGGSLRLSCAASGSTFS FNAMG      49

WYRQVPGKQRELVA AIGNDGATYYVDSVK            97

GRFTIARENAKNTVYLQMSSLKPEDTAVYYCKG

RGGLTQYSEHDY WGQGTQVTVSS EPKTPFKPQP       129

HGL#8 (SEQ ID NO: 29)
QVQLQESGGGLVQTGGSLRLSCAASGSIGS MYVLS      49

WYRQAPGKQREPVA ALMGSGSTTYADSVK            97

GRFTISRDNIKNTMYLQMNSLTPEDTGVYYCAG

TGAEGHY WGQGTQVTVSS AHHSEDPSS             124

HGL#9 (SEQ ID NO: 30)
QVQLQESGGGLVQAGGSLRLSCAASGSIGS LYVMS      49

WYRQAPGKQREPVA ALMGSGSTTYADSVK            97

GRFTISRDNIKNTMYLQMNSLKPEDTGVYYCAG

TGAEGHY WGQGTQVTVSS EPKTPKPQP             124

HGL#10 (SEQ ID NO: 31)
QVQLQESGGDLVQAGGSLRLACAASGSTFS FNAMG      49

WYRQVPGKQRELVA AIGNDGSTYYVNSVK            97

GRFTTSRENAKNTVYLQMNSLKPEDTAVYYCKG

RGGLTQYSEHDY WGQGTQVTVSS EPKTPKPQP        129

HGL#11 (SEQ ID NO: 32)
QVQLQESGGGLVQAGGSLRLSCTASGTTDN INAMG      49

WYRQAPGKQRELVA AISSGGDTYYTEFVK            97

GRFTISRDNAKKAVYLQMNNLKSEDTAVYSCKM
```

-continued

```
TDMGRYGTSEW WGQGTQVTVSS EPKTPKPQP         128

HGL#15 (SEQ ID NO: 33)
QVQLQESGGGLVQAGGSLRLSCAASGSTG SMYVMS       49

WYRQAPGKEREPIA AIMGSGSTTYADSVK             97

GRFTISRDNEKNTMYLQMNSLTPEDTGVYYCAG

TGAEGHY WGQGTQVTVSS EPKTPKPQP             124

HGL#16 (SEQ ID NO: 34)
QVQLQESGGGLVQAGGSLRLSCAASGSDFR YNAMA       49

WYRQAPGKQRKLVA TITYTYRTNYADSVK             97

GRFTISRDNARGTVYLQMNSLKPEDTAVYYCAA

AASLELTPTSYDY WGQGTQVTVSS EPKTPKPQP       130
```

From clones HGL#1(SEQ ID NO: 27), HGL#8(SEQ ID NO: 29), HGL#9(SEQ ID NO: 30), HGL#10(SEQ ID NO: 31), HGL#11 (SEQ ID NO: 32) and HGL#16 (SEQ ID NO: 34) the $V_HH$ encoding gene fragments were digested with PstI and BstEII from the phage display vector pUR5071. The DNA fragments were cloned into the episomal S. cerevisiae plasmid pUR4547, which drives the secretion of $V_HH$ domains without any tags. In this way pUR5251, pUR5252, pUR5253, pUR5254, pUR5255, pUR5256 were obtained encoding the $V_HH$ domains of clones HGL#1(SEQ ID NO: 27), HGL#8(SEQ ID NO: 29), HGL#9(SEQ ID NO: 30), HGL#10(SEQ ID NO: 31), HGL#11 (SEQ ID NO: 32) and HGL#16 (SEQ ID NO: 34) respectively. The PstI/BstEII fragments were also cloned into the episomal S. cerevisiae plasmid pUR4585, which is responsible for the secretion of the $V_HH$ domain containing a myc- and a hexahistidine tag at its carboxy-terminus. The clones coded pUR5257, pUR5258, pUR5259, pUR5260, pUR5261 and pUR5262 were obtained containing the $V_HH$ encoding inserts of clones HGL#1(SEQ ID NO: 27), HGL#8(SEQ ID NO: 29), HGL#9(SEQ ID NO: 30), HGL#10(SEQ ID NO: 31), HGL#11 (SEQ ID NO: 32) and HGL#16 (SEQ ID NO: 34) respectively.

Using 12 ml of culture supernatant from the induced clones containing the hexahistidine tag the $V_HH$ fragments were purified with IMAC (according to the method described in paragraph 3.2). The yield was determined by measuring the optical density at 280 nm using the calculated molar extinction coefficient.

The efficiency of HGL recognition was determined for each individual antibody with ELISA using indirectly coated enzyme (FIG. 4A) and the degree of inhibition with the enzyme assay (FIG. 4B).

4.3 Measurement of Inhibition in Intestinal Juices.

The measurement of the inhibition properties of the antibodies in accordance to the invention can be carried out in accordance to the method described in Carriere et al in Gastroenterology 1993:105:876-888.

Example 5

Effect of Anti Lipase $V_H$Hs on Triglyceride and Fatty Acid Uptake In Vivo

The antibodies anti-HGL8 (example 4) and anti-HPL18 (example 3) were tested for inhibition of fat uptake in an animal model. To ensure maximal lipase inhibition in this initial test, the gastric and pancreatic lipase inhibitors were tested in combination.

Figure 5:
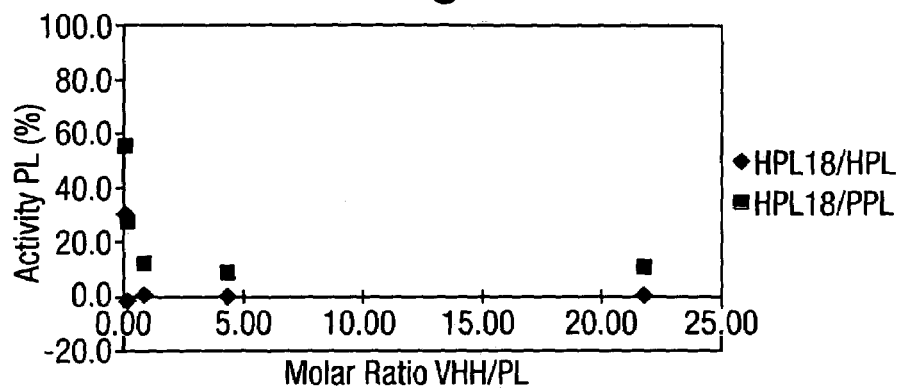
FIG. 5 shows the cross-reactivity of HPL18 with PPL.

Cross reactivity of anti-HPL18 with porcine pancreatic lipase (PPL) was tested (FIG. 5). Instead of the HPL standard delivered with the lipase assay, PPL (Fluka no 62300; lipase from hog pancreas; 20 U/mg) was used. The lipase was dissolved in PBS (4 mg/ml) and centrifuged (2 min, 15600×g). The supernatant was diluted (70 µl supernatant+930 µl PBS) and used as PPL standard as described for HPL. Cross reactivity of anti-HGL8 with porcine gastric lipase was tested by western blotting using pig gastric extracts.

Male piglets of approximately 15 Kg were fed with differing amounts of anti-HGL and anti-HPL antibodies as part of a high fat diet. As a control, each animal also received a diet without antibody fragment addition. The antibody fragment dosage was chosen such that there was sufficient antibody present to inhibit all of the gastric or pancreatic lipase, based on the assumption that the piglets produced approximately the same amount of GI tract lipase as humans: 25 mg HGL and 250 mg HPL per meal. As the in vivo stability of the antibody fragments was not known, a second dosage of antibody fragment was chosen based on an excess of fragment with respect to lipases.

Jugular catheters were inserted under anesthesia in three approximately 15 kg male piglets. The piglets were allowed 6 days to recover. During this time they were fed 120 g twice daily (bigbatterikorrel ID-Lelystad, The Netherlands). On the afternoon preceding the serving of the test food, the feed was limited to 60 g. To allow the piglets to accustom to additional yeast extract in their diets, after day 2 the feed was supplemented by addition of a S. cerevisiae fermentation supernatant derived from S. cerevisiae gal1LEU (a prototrophic strain which does not express lipase inhibiting antibody fragments) to al level of 4%. Also after day 2 the fat level in the feed was increased by the addition of 5% sunflower oil (C1000).

The antibodies were prepared from the supernatants of the appropriate S. cerevisiae transformants by concentration with a dialysis unit (Hemophan fiber dialyzer GFSplus 12, Gambro, Breda) followed by freeze drying. The antibody concentration was adjusted such that the feed could be prepared by addition of 10 ml of antibody containing solution. The dosages of antibodies given are shown in table 1.

TABLE 5.1

| | The feeding regime for the addition of antibody fragments. | | |
|---|---|---|---|
| Day | Animal 1 (15.6 Kg) | Animal 2 (13.1 Kg) | Animal 3 (11.9 Kg) |
| 1 | 0 mg/250 g feed | αHPL18 400 mg/ 250 g feed + αHGL8 80 mg/ 250 g feed | αHPL18 80 mg/ 250 g feed + αHGL8 16 mg/ 250 g feed |
| 3 | αHPL18 80 mg/250 g feed + αHGL8 16 mg/250 g feed | 0 mg/250g feed | αHPL18 400 mg/ 250 g feed + αHGL8 80 mg/ 250 g feed |
| 5 | αHPL18 400 mg/ 250 g feed + αHGLB 80 mg/ 250 g feed | αHPL18 80 mg/ 250 g feed + αHGL8 16 mg/ 250 g feed | 0 mg/250 g feed |

Blood samples were collected from a jugular catheter at 30 minute intervals extending from 1-6 hours after feeding. As is common for these types of studies (Reitzma et al, 1994), the total quantity of triglyceride (TG) was determined as the area under the curve of TG or FFA concentration with respect to time. In this way the cumulative concentration of the 11 time points between 1-6 hours was measured. The results are shown in table 2.

TABLE 5.2

Cumulative concentrations of triglyceride (TG) in postprandial plasma (1-6 h) in absolute values and as percentage of the control.

| Test meal | Animal 1 | Animal 2 | Animal 3 |
|---|---|---|---|
| Control | 4.60 mM (100%) | 3.19 mM (100%) | 4.68 mM (100%) |
| Estimated optimum $V_HH$ concentration | 3.88 mM (84%) | 2.66 mM (83%) | 4.93 mM (105%) |
| $V_HH$ excess | 2.68 mM (58%) | 2.68 mM (84%) | 4.90 mM (105%) |

In two of the three animals, there was a marked reduction in blood triglyceride levels when the animals received feed containing the lipase inhibiting antibody combination in comparison to the control meal. This indicates that the antibodies indeed inhibited fat digestion and uptake.

The invention claimed is:

1. An antibody, or fragment thereof, wherein the antibody or fragment thereof is capable of binding specifically to human pancreatic lipase, said antibody or fragment thereof comprising a heavy chain variable domain derived from an immunoglobulin naturally devoid of light chains, and wherein the antibody, or fragment thereof, is selected from the group consisting of the following sequences: HPL#11 (SEQ ID NO: 18), HPL#12 (SEQ ID NO: 19), HPL#13 (SEQ ID NO: 20), HPL#14 (SEQ ID NO: 21), HPL#15 (SEQ ID NO: 22), HPL#18(SEQ ID NO: 23), HPL#19 (SEQ ID NO: 24), HPL#22 (SEQ ID NO: 25) and HPL#30 (SEQ ID NO: 26).

2. Food product comprising the antibody or fragment thereof in accordance with claim 1.

3. Pharmaceutical product comprising the antibody or fragment thereof in accordance with claim 1.

* * * * *